(12) United States Patent
Amundsen

(10) Patent No.: US 7,780,441 B2
(45) Date of Patent: Aug. 24, 2010

(54) MOUNTING DEVICE FOR ORTHODONTIC RETAINER ELEMENTS AND A METHOD OF MAINTAINING SAID ELEMENTS IN PLACE FOR MOUNTING ON CORRESPONDING TEETH

(76) Inventor: Ole C. Amundsen, Volstadveien 68 C, Stavanger (NO) N-4025

( * ) Notice: Subject to any disclaimer, the term of this patent is extended or adjusted under 35 U.S.C. 154(b) by 1178 days.

(21) Appl. No.: 11/111,278

(22) Filed: Apr. 21, 2005

(65) Prior Publication Data
US 2006/0240373 A1    Oct. 26, 2006

(51) Int. Cl.
*A61C 3/00* (2006.01)
(52) U.S. Cl. .............................................. 433/3; 433/18
(58) Field of Classification Search .................... 433/3, 433/9–11, 18, 20, 24, 215
See application file for complete search history.

(56) References Cited

U.S. PATENT DOCUMENTS

| 2,150,005 | A | | 3/1939 | McNinch | |
|---|---|---|---|---|---|
| 3,984,915 | A | | 10/1976 | Noble et al. | |
| 4,202,328 | A | * | 5/1980 | Sukkarie | 433/18 |
| 4,311,463 | A | | 1/1982 | Glattly | |
| 4,384,854 | A | * | 5/1983 | Garfinkel | 433/215 |
| 4,504,229 | A | * | 3/1985 | Garito et al. | 433/215 |
| 4,508,505 | A | | 4/1985 | Smiley et al. | |
| 4,609,350 | A | | 9/1986 | Krause | |
| 4,968,248 | A | * | 11/1990 | McColgan et al. | 433/18 |
| 5,791,896 | A | * | 8/1998 | Ipenburg | 433/3 |
| 6,071,121 | A | * | 6/2000 | Simon | 433/37 |
| 6,257,884 | B1 | * | 7/2001 | Chang | 433/18 |
| 2003/0124478 | A1 | * | 7/2003 | Amundsen | 433/18 |

FOREIGN PATENT DOCUMENTS

| DE | 2753640 | 6/1978 |
|---|---|---|
| GB | 2236953 | 4/1991 |
| WO | WO-0182821 | 11/2001 |

* cited by examiner

*Primary Examiner*—Cris L Rodriguez
*Assistant Examiner*—Matthew M Nelson
(74) *Attorney, Agent, or Firm*—Andrus, Sceales, Starke & Sawall, LLP

(57) ABSTRACT

The invention concerns a mounting device for a pair of orthodontic retainer elements intended for attachment to a pair of adjacent teeth in a dental arch during passive orthodontic treatment. The retainer elements include approximal surfaces formed complementary to each other so as to form contact surfaces capable of stabilizing each other when the pair of retainer elements is attached to the pair of adjacent teeth, thereby also stabilizing the pair of teeth. The mounting device comprises a jig to which the pair of retainer elements is releasably connected and is maintained in a specific spatial relationship, which allows the approximal surfaces to form the stabilizing contact surfaces when mounted on the pair of teeth. The invention also concerns a method of maintaining a correct spatial relationship between the pair of retainer elements, especially when attaching them to the pair of teeth.

24 Claims, 12 Drawing Sheets

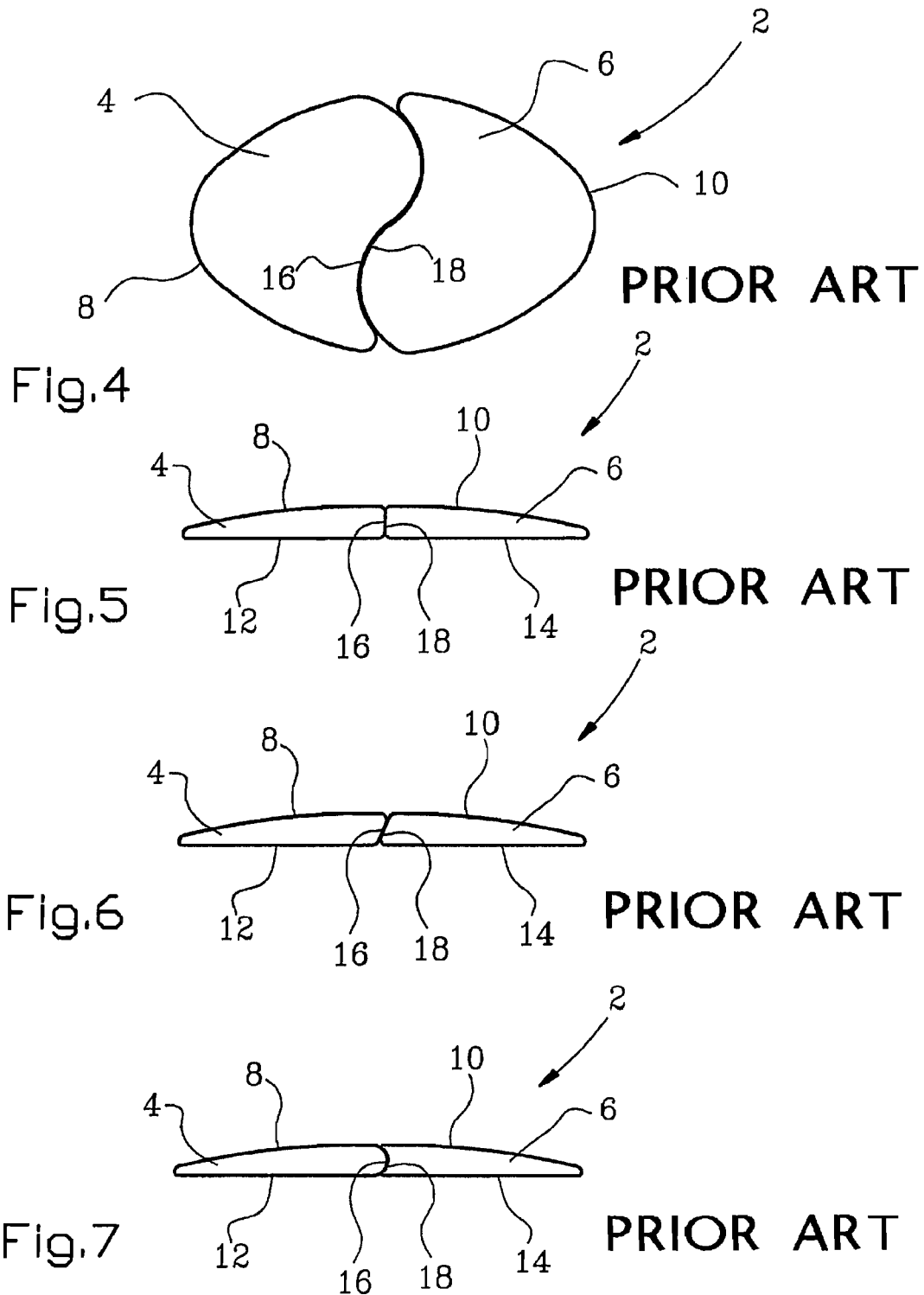

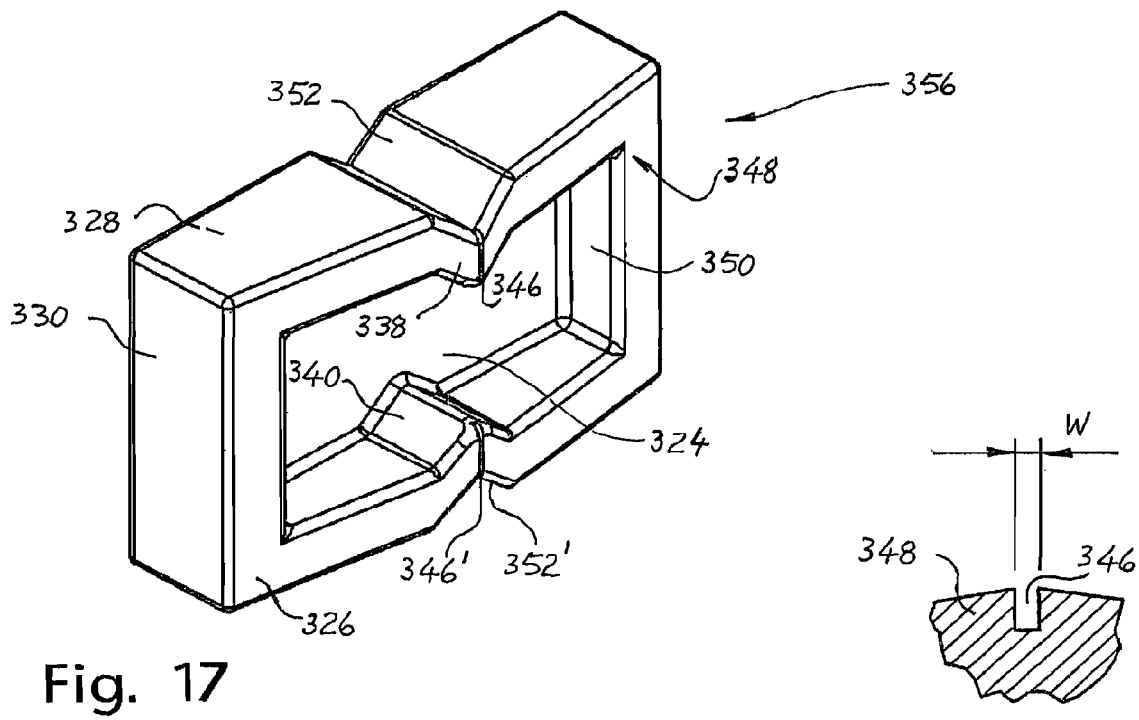
Fig. 17
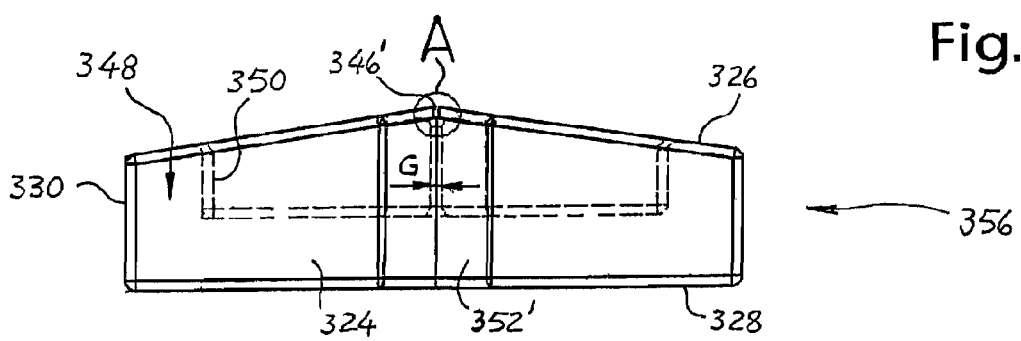
Fig. 19
Fig. 18
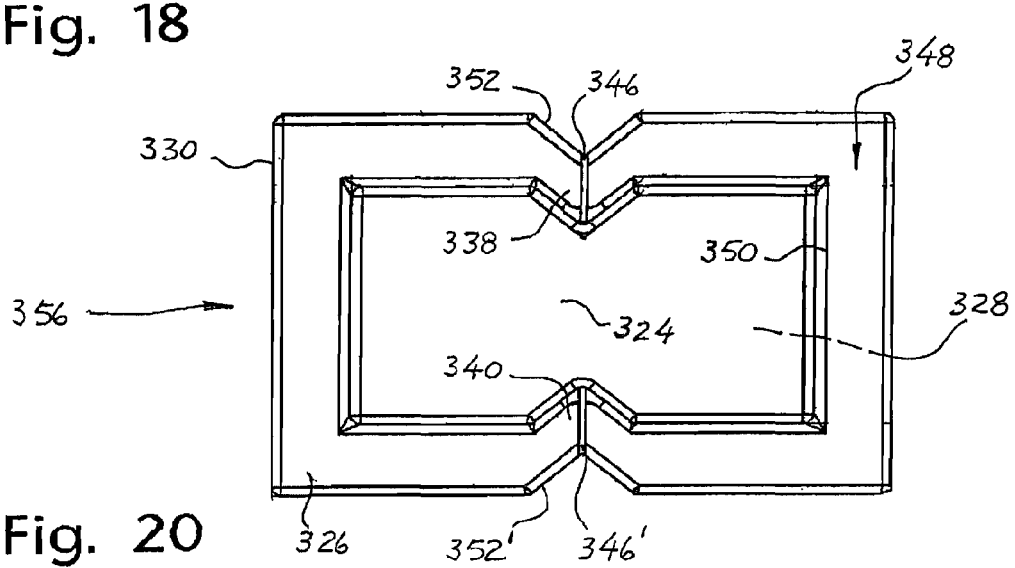
Fig. 20

MOUNTING DEVICE FOR ORTHODONTIC RETAINER ELEMENTS AND A METHOD OF MAINTAINING SAID ELEMENTS IN PLACE FOR MOUNTING ON CORRESPONDING TEETH

BACKGROUND OF THE INVENTION

The present invention concerns a mounting jig for a pair of orthodontic retainer elements. During orthodontic treatment, the pair of retainer elements is intended for retaining, i.e. stabilizing, a pair of adjacent teeth relative to each other in a dental arch of a patient. As such, at least one pair of adjacent teeth may be stabilized in the patient's mandible (lower jaw) and/or maxilla (upper jaw). The purpose of the mounting jig is to maintain mechanically a correct spatial relationship between the two retainer elements in a pair thereof, particularly in the process of attaching the retainer elements to the adjacent teeth of the patient.

The present invention also concerns a method of maintaining a correct spatial relationship between the retainer elements in a pair thereof, particularly in the process of attaching the retainer elements to the adjacent teeth.

Orthodontic treatment generally includes a period of active treatment and a period of passive treatment. During the period of active treatment, incorrectly placed teeth are moved into correct dental positions in the patient's mouth. During the subsequent period of passive treatment, i.e. the retention period, the previously corrected teeth are to be retained in their correct dental positions using some type of dental retainer apparatus. In the retention period, orthodontic patients must wear a suitable retainer apparatus during at least a part of a day for extended periods of time, up to several years.

Retainer apparatuses according to prior art typically include removable retainers and fixed retainers.

A removable retainer may be comprised of a plastic-based retainer plate, which is oftentimes combined with steel braces and steel clamps. The removable retainer is normally used during at least a part of the day, for example when the patient sleeps. The patient therefore must learn to use and maintain the retainer plate correctly during the retention period. This, however, requires persistent action from the patient, which may prove difficult to maintain should the patient not be willing or able to do so. Moreover, a retainer plate may also lose its ability over time to maintain the teeth in their corrected dental positions, hence being inaccurate, and some tooth remobilization therefore may take place. Moreover, a retainer plate may be uncomfortable to wear and also be prone to break easily. For these reasons, removable retainer plates are unsuitable for orthodontic retention treatments lasting several years.

A fixed retainer, however, may be comprised of an orthodontic wire, also termed a retention wire. The wire is cut into appropriate lengths and adapted for the teeth requiring dental correction. A suitable dental bonding material, for example a composite material, glue or a soldering agent, is used to attach the wire directly and continuously onto the appropriate teeth. Alternatively, the fixed retainer may be comprised of an integrally molded brace attached to a bar provided with retention base fasteners that are secured to the teeth by means of a suitable bonding material. Inasmuch as a retention wire extends continuously from tooth to tooth when attached thereon, however, a fixed retainer typically obstructs the access openings between the teeth thus affected, hence obstructing the patient's ability to maintain proper dental hygiene in this dental region when using, for example, dental floss or toothpicks. This obstructing nature may have adverse effects on the patient's teeth and/or gums and also on the retainer apparatus. As such, use of dental-hygienic means may cause inadvertent detachment of some or all of the retainer apparatus from the teeth. Moreover, dental hygiene may be difficult to perform in this dental setting. Furthermore, detrimental deposits of plaque and tartar may form in response to insufficient or lacking dental hygiene.

Patent publication WO 01/82821, which corresponds to patent application PCT/NO01/00174 of Amundsen, also discloses a dental retainer device for stabilization of a pair of teeth, or groups of such pairs, in a mandible and/or a maxilla of a patient during a retention period of orthodontic treatment.

The retainer apparatus of Amundsen is comprised of a pair of individual retainer elements intended to cooperate through mutual contact when in position of use. The elements may be formed from a material suitable for dental use, for example metal, porcelain or plastics materials. In this position, each retainer element is secured individually to a corresponding dental attachment surface of one of the two adjacent teeth in the same dental arch. For securing thereof, a bonding agent such as a composite material may be used. Each retainer element is comprised of a so-called outer surface, a basal surface and an approximal surface. The two resulting approximal surfaces are formed complementary to each other. When in position of use, the two approximal surfaces provide mutual contact surfaces that are in cooperating contact and thus stabilize each other and the associated pair of teeth to which they are attached. The approximal surfaces may be of a plane shape or have some other suitable surface shape, for example a curved surface shape. As such, the approximal surfaces may have a surface shape allowing the two retainer elements to interlock when assembled in their position of use on the two corresponding, adjacent teeth.

The pair of retainer elements may also have an elliptical or rounded and rectangular circumference shape when placed in position of use on corresponding teeth. Moreover, the outer oral surface of each retainer element may be smooth and/or rounded to feel comfortable when worn on the patient's teeth.

Furthermore, the retainer elements may also be releasably attached to an applicator strip or guide strip intended for insertion between the adjacent teeth for securing the retainer elements to the teeth. This facilitates the fitting of the retainer elements onto the patient's teeth.

In view of the prior art mentioned above, the retainer apparatus of Amundsen advantageously is well suitable for long-term orthodontic retention treatment, also allowing proper dental hygiene to be carried out without jeopardizing the integrity of the apparatus. Thus, for example, dental floss may easily be applied between the retainer elements.

One disadvantage of the retainer apparatus of Amundsen, however, is the small size and two-component nature of the apparatus. This disadvantage may also apply when a guide strip is used for attaching the pair of retainer elements onto the corresponding pair of teeth. When using a guide strip, preferably the approximal surface of a retainer element is attached on either side of the strip. Upon applying the retainer elements to the corresponding teeth, some misalignment may arise between the retainer elements as they are released from the guide strip and attached to the teeth. Moreover, it may prove somewhat cumbersome to properly control the amount and positioning of dental bonding material used between the retainer elements and the teeth. These problems may require subsequent and immediate remedial actions. As such, some immediate repositioning of the retainer elements may be necessary after attachment to the teeth and prior to hardening of the bonding material. Furthermore, some of the bonding material may have to be removed from the retainer elements and/or the teeth to ensure proper functioning of the retainer apparatus thereafter.

A further need therefore exists for a device and a method for improving the precision and efficiency of attaching the pair of retainer elements onto the pair of teeth, which is the main object of the present invention.

SUMMARY OF THE INVENTION

In one aspect, the present invention is directed at a mounting device for a pair of orthodontic retainer elements intended for attachment to a pair of adjacent teeth in a dental arch in a mouth of a patient during passive orthodontic treatment. Each such retainer element includes a dental attachment surface, an approximal surface and an oral surface. The dental attachment surface of one retainer element is intended for attachment to one of the adjacent teeth, whereas the dental attachment surface of the other retainer element is intended for attachment to the other of the adjacent teeth. At least one portion of the approximal surface of one retainer element is formed complementary to at least one portion of the approximal surface of the other retainer element. Thereby, said two approximal surface portions form adjacent contact surfaces that will mutually cooperate to support and stabilize each other when the pair of retainer elements is attached to the pair of adjacent teeth in the dental arch, thus also stabilizing the adjacent teeth. According to the present invention, said mounting device comprises:
- a jig to which the pair of retainer elements is releasably connected; and
- wherein the pair of retainer elements is maintained mechanically in a specific spatial relationship relative to each other, said spatial relationship defined as the spatial relationship required between the pair of retainer elements when mounted on the pair of adjacent teeth.

The retainer elements may be formed from a material suitable for dental use, for example metal, porcelain, plastics materials or alike. The jig may also be formed from such materials.

If required, both the mandible and the maxilla may be provided simultaneously with such pairs of retainer elements. Moreover, several pairs of such elements may be used in the same dental arch, preferably assembled in one or more retention segments. Each retention segment may be comprised of several pairs of retainer elements aligned successively along the dental arch, thereby stabilizing successive teeth in the dental arch. Use of such retention segments is further detailed in WO 01/82821 of Amundsen.

In a preferred embodiment of the present mounting device, the jig may be comprised of one of:
- a base having a dental side, an oral side and an external perimeter side, wherein at least one portion of the oral surface of each retainer element is releasably connected to the dental side of said base;
- a rim wall enclosure having a perimeter side, an internal side, a dental side and an oral side, wherein at least one portion of the oral surface of each retainer element is releasably connected within said rim wall enclosure; and
- a socket comprising an assembly of said base and said rim wall enclosure, wherein the rim wall enclosure projects from said dental side of the base and is connected along the perimeter thereof.

A skilled orthodontic practisioner may use dental tools common in the art to manually attach the jig with its pair of retainer elements to the pair of teeth.

More preferably, however, the above embodiments of a jig with its pair of retainer elements may be releasably connected to a suitable applicator device, said applicator device intended for insertion into the mouth of the patient for attaching the pair of retainer elements to the pair of adjacent teeth therein. Such an applicator device may facilitate the attachment operation.

Furthermore, the applicator device may be comprised of an elongated holding device capable of holding the jig releasably connected thereto.

Advantageously, the jig with its pair of retainer elements may be releasably connected to an applicator device comprised of a guide strip intended for insertion, at least partially, between the adjacent teeth for attaching the pair of retainer elements thereto;
- wherein the guide strip is provided with an opening through which the jig with its pair of retainer elements extends transversely relative to a longitudinal axis of the guide strip; and
- wherein one retainer element is positioned on either side of said longitudinal axis, at least when the pair of retainer elements is attached to the pair of adjacent teeth.

Typically, the guide strip may be formed from a resilient material, including steel and plastics materials.

Naturally, said opening in the guide strip must correspond to the external shape of the jig when provided with the pair of retainer elements therein. Locating a retainer element on either side of said longitudinal axis ensures that the element will be located vis-à-vis a corresponding tooth when the guide strip is inserted, at least partially, between the adjacent teeth in a pair thereof, and when the pair of retainer elements has been pulled towards the pair of adjacent teeth.

In order to facilitate the positioning of one retainer element on either side of said longitudinal axis of the guide strip, the guide strip may be provided with at least one locking tab extending into said opening therein;
- wherein the jig, at said perimeter side thereof, is provided with a corresponding recess within which the locking tab is engaged; and
- wherein the recess is positioned vis-à-vis the adjacent approximal surface portions of the retainer elements.

Similar to the guide strip, also the locking tab may be formed from a resilient material. Preferably, the locking tab is integral to the guide strip. As such, the locking tab and the opening may be punched out simultaneously in a one-step operation using a correspondingly shaped punching tool. This structural configuration allows the locking tab to flex when inserting the jig into the guide strip opening, subsequently snapping into the external recess to interlock with the jig.

In order to further facilitate the positioning of one retainer element on either side of said longitudinal axis of the guide strip, said jig, at the dental side thereof, may be provided with a groove within which the guide strip is engaged and interlocks; and
- wherein the groove is positioned vis-à-vis said longitudinal axis of the guide strip and extends therealong.

Advantageously, the groove is provided with a width substantially equal to a thickness of the guide strip.

Besides facilitating positioning of the retainer elements, said groove advantageously restrain excess dental bonding material from entering into crevices in regions between the retainer elements and also between the jig and the elements. Providing the present jig with said groove may be additional to, or in replacement of, the above-mentioned recess provided at the perimeter side of the jig. The recess allows interlocking engagement between the guide strip and the perimeter side of the jig, whereas the groove allows interlocking engagement between the guide strip and the dental side of the jig.

Two adjacent teeth in a dental arch are commonly in contact with each other, at least parts thereof. When inserting a guide strip between the two adjacent teeth, the teeth are subjected to a wedging force that causes them to yield and temporarily move apart. Due to their inherent resiliency and physiological mobility within their gum, the two adjacent teeth will set up an equal reaction force in response to the wedging force. Once the guide strip is removed the reaction force is unleashed, causing the adjacent teeth to rebound and move towards each other until they engage, at least partially.

In position of use, however, the pair of retainer elements is attached to the pair of adjacent teeth. This implies that also the retainer elements will follow the rebounding path of the teeth and move towards each other until they engage, at least partially. When in this contact position, substantially all of said reaction force ideally should be expended. Should the space between the elements not correspond to the space between the adjacent teeth when wedged apart, however, the reaction force will be expended prematurely or inadequately when the approximal surfaces of the retainer elements engage each other. This situation of discrepancy may have adverse effects on the retainer elements, the teeth to which they are attached and/or on the bonding material between them.

As mentioned, at least portions of the approximal surfaces of the retainer elements are to bear against each other for the purpose of supporting and stabilizing each other and the teeth to which they are attached. The distance between said approximal surfaces therefore must be adapted so as to provide an appropriate interaction between the elements after the guide strip has been removed and the corresponding, adjacent teeth have relaxed in their gum. Accordingly, it is important to choose a proper distance at which the approximal surfaces are spaced apart while being maintained mechanically in said specific spatial relationship relative to each other in the jig.

In general, an excessive distance will provide inadequate mutual support and stabilization between the retainer elements, whereas a deficient distance will allow an excessive reaction force to act between the elements and potentially cause structural damage to the retainer elements, the corresponding teeth and/or the bonding material between them.

In a preferred embodiment of the present mounting device, the approximal surfaces of the retainer elements may be spaced apart in the jig at a distance substantially equal to a thickness of the guide strip. For most patients, this distance will ensure proper non-destructive interaction between the elements when the associated teeth are relaxed during passive orthodontic treatment.

Furthermore, the jig may be provided with at least one tapered projection extending within the perimeter side of the jig;
  wherein said projection is positioned vis-à-vis the adjacent approximal surface portions of the retainer elements; and
  wherein each side of the projection is engaged with a corresponding bevel edge of the approximal surface of each retainer element.

When the jig is comprised of or includes said rim wall enclosure, said internal side thereof may be provided with at least one such tapered projection extending within the rim wall enclosure.

The tapered projection may serve as a divider between the two retainer elements, simultaneously spacing said approximal surfaces of the retainer elements apart at a proper distance. Also, the tapered projection is formed to fit a bevel edge of the approximal surface edge of each retainer element. In position of use, the approximal surface bevel edge of one retainer element is juxtaposed relative to the approximal surface bevel edge of the other retainer element. This structural configuration of bevel edges facilitates insertion of, for example, dental floss between the retainer elements and the adjacent teeth to which they are attached, which facilitates the dental hygiene for the patient during orthodontic treatment.

Advantageously, each retainer element may be releasably connected to the jig by means of at least one of;
  an adhesive agent, including tape;
  a breakable connection means;
  at least one connecting pin; and
  at least one snap connector.

Other suitable and releasable connection means may also be used.

Moreover, any suitable combination of the above-mentioned features of the present mounting device may be used, thereby facilitating the subsequent attachment of said pair of retainer elements to said pair of adjacent teeth in the patient's mouth.

In another aspect, the present invention is directed at a method of maintaining mechanically a pair of retainer elements in a specific spatial relationship relative to each other, said retainer elements intended for attachment to a pair of adjacent teeth in a dental arch in a mouth of a patient during passive orthodontic treatment. Each such retainer element includes a dental attachment surface, an approximal surface and an oral surface. The dental attachment surface of one retainer element is intended for attachment to one of the adjacent teeth, whereas the dental attachment surface of the other retainer element is intended for attachment to the other of the adjacent teeth. At least one portion of the approximal surface of one retainer element is formed complementary to at least one portion of the approximal surface of the other retainer element. Thereby, said two approximal surface portions form adjacent contact surfaces that will mutually cooperate to support and stabilize each other when the pair of retainer elements is attached to the pair of adjacent teeth in the dental arch, thus also stabilizing the adjacent teeth. According to the present invention, said method comprises the steps of:
  releasably connecting the pair of retainer elements to a jig; and
  maintaining the pair of retainer elements in a specific spatial relationship relative to each other in the jig, said spatial relationship defined as the spatial relationship required between the pair of retainer elements when mounted on the pair of adjacent teeth.

In a preferred embodiment, the present method may further comprise the step of releasably connecting the pair of retainer elements to one of:
  a base having a dental side, an oral side and a perimeter side, releasably connecting at least one portion of the oral surface of each retainer element to the dental side of said base;
  a rim wall enclosure having a perimeter side, an internal side, a dental side and an oral side, releasably connecting at least one portion of the oral surface of each retainer element within the rim wall enclosure; and
  a socket comprising an assembly of said base and said rim wall enclosure, wherein the rim wall enclosure projects from said dental side of the base and is connected along the perimeter thereof, releasably connecting at least one portion of the oral surface of each retainer element within the socket.

More preferably, the method may further comprise the step of releasably connecting the jig with its pair of retainer elements to an applicator device, said applicator device intended for insertion into the mouth of the patient for attaching the pair of retainer elements to the pair of adjacent teeth therein.

Furthermore, the method may further comprise the step of providing the applicator device in the form of an elongated holding device capable of holding the jig releasably connected thereto.

Advantageously, the method may further comprise the steps of:
  releasably connecting the jig with its pair of retainer elements to an applicator device in the form of a guide strip intended for insertion, at least partially, between the adjacent teeth for attaching the pair of retainer elements thereto;
  providing the guide strip with an opening through which the jig with its pair of retainer elements extends transversely relative to a longitudinal axis of the guide strip; and
  positioning one retainer element on either side of said longitudinal axis.

In order to facilitate the positioning of one retainer element on either side of said longitudinal axis of the guide strip, the method may further comprise the steps of:
  providing the guide strip with at least one locking tab extending into said opening therein;
  providing the jig, at said perimeter side thereof, with a corresponding recess;
  positioning the recess vis-à-vis the adjacent approximal surface portions of the retainer elements; and
  engaging the locking tab within the recess.

Preferably, the locking tab is provided integrally to the guide strip.

In order to further facilitate the positioning of one retainer element on either side of said longitudinal axis of the guide strip, the method may further comprise the steps of:
  providing said jig, at the dental side thereof, with a groove;
  positioning the groove vis-à-vis said longitudinal axis of the guide strip and extends therealong; and
  engaging and interlocking the guide strip within the groove.

Advantageously, the method may comprise a step of providing the groove with a width substantially equal to a thickness of the guide strip.

The step of providing the present jig with said groove may be additional to, or in replacement of, the above-mentioned step of providing a recess at the perimeter side of the jig.

In a preferred embodiment, the method may further comprise the step of spacing the approximal surfaces of the retainer elements apart in the jig at a distance substantially equal to a thickness of the guide strip.

Furthermore, the method may further comprise the steps of:
  providing said jig with at least one tapered projection extending within the perimeter side of the jig;
  positioning said projection vis-à-vis the adjacent approximal surface portions of the retainer elements; and
  engaging each side of the projection with a corresponding bevel edge of the approximal surface of each retainer element.

When the jig is comprised of or includes said rim wall enclosure, the method may comprise the step of providing said internal side thereof with at least one such tapered projection extending within the rim wall enclosure.

Advantageously, the method may further comprise the step of releasably connecting each retainer element to the jig by means of at least one of:
  an adhesive agent, including tape;
  a breakable connection means;
  at least one connecting pin; and
  at least one snap connector.

Moreover, any suitable combination of the above-mentioned steps may be used to maintain mechanically the pair of retainer elements in a specific spatial relationship relative to each other, thereby facilitating their subsequent attachment to said pair of adjacent teeth in the patient's mouth.

In the following, non-limiting examples of embodiments of the claimed mounting jig for a pair of orthodontic retainer elements will be shown.

BRIEF DESCRIPTION OF THE DRAWINGS

The following drawings are schematic and may be somewhat distorted with respect to sizes and relative dimensions. The same reference numeral will represent the same detail or feature in each drawing where it is shown, in which:

FIGS. 1-4 show plan views of various embodiments of pairs of orthodontic retainer elements as disclosed in prior art of Amundsen, and each pair of elements is shown in its position of use whilst assembled and having an elliptical circumference shape;

FIGS. 5-7 show front views of various embodiments of the pairs of retainer elements shown in FIGS. 1-4, and FIGS. 5-7 show different shapes of mutually supporting, complementary approximal surfaces of a pair of the retainer elements whilst in position of use;

FIG. 17 shows a perspective view of an embodiment of the mounting jig according to the present invention, wherein the jig is in the form of a socket comprising an assembly of a base and a rim wall enclosure;

FIG. 18 shows a front view of the jig according to FIG. 17, dashed lines defining an inner space within the jig for releasably attaching a pair of retainer elements, FIG. 18 also showing a circle section A;

FIG. 19 shows an enlarged view of section A of FIG. 18 showing a groove provided in the rim wall enclosure of the jig;

FIG. 20 shows a plan view of the jig according to FIGS. 17 and 18;

DETAILED DESCRIPTION OF EMBODIMENTS OF THE INVENTION

Figure 1:
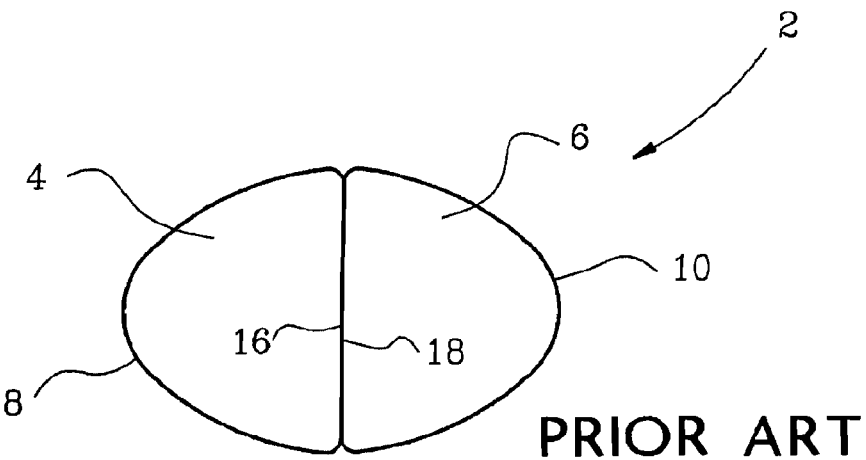
Figure 2:
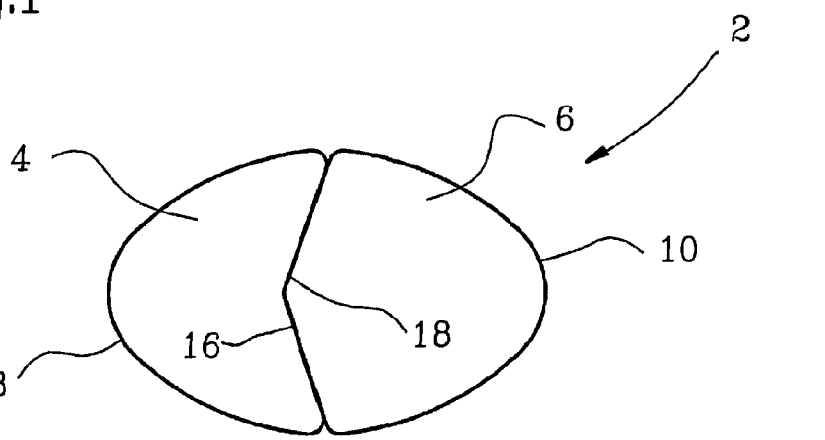
Figure 3:
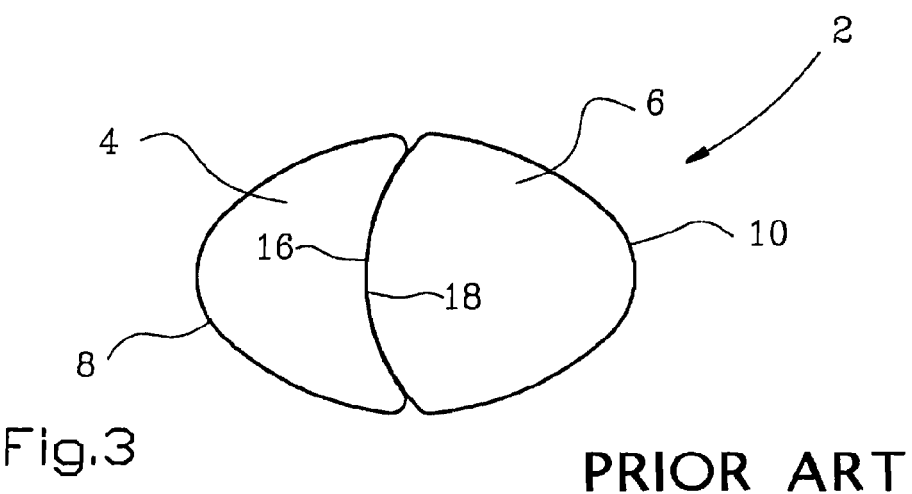
Figure 8:
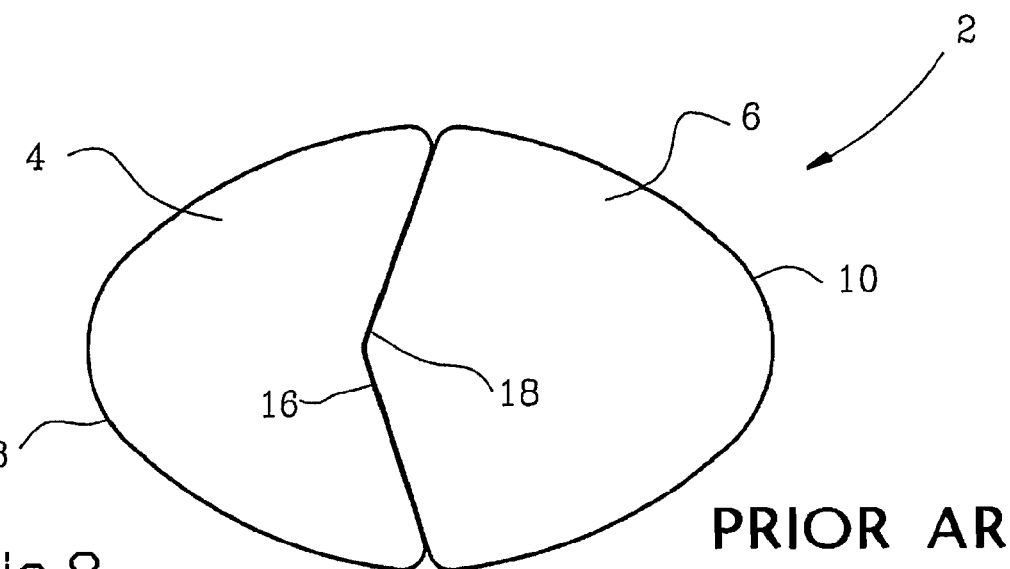
FIGS. 8 and 9 show the pair of retainer elements of FIG. 2 in larger scale when in assembled view and exploded view, respectively, the exploded view clearly showing the complementary shape the two approximal surfaces of the pair of retainer elements.
Figure 9:
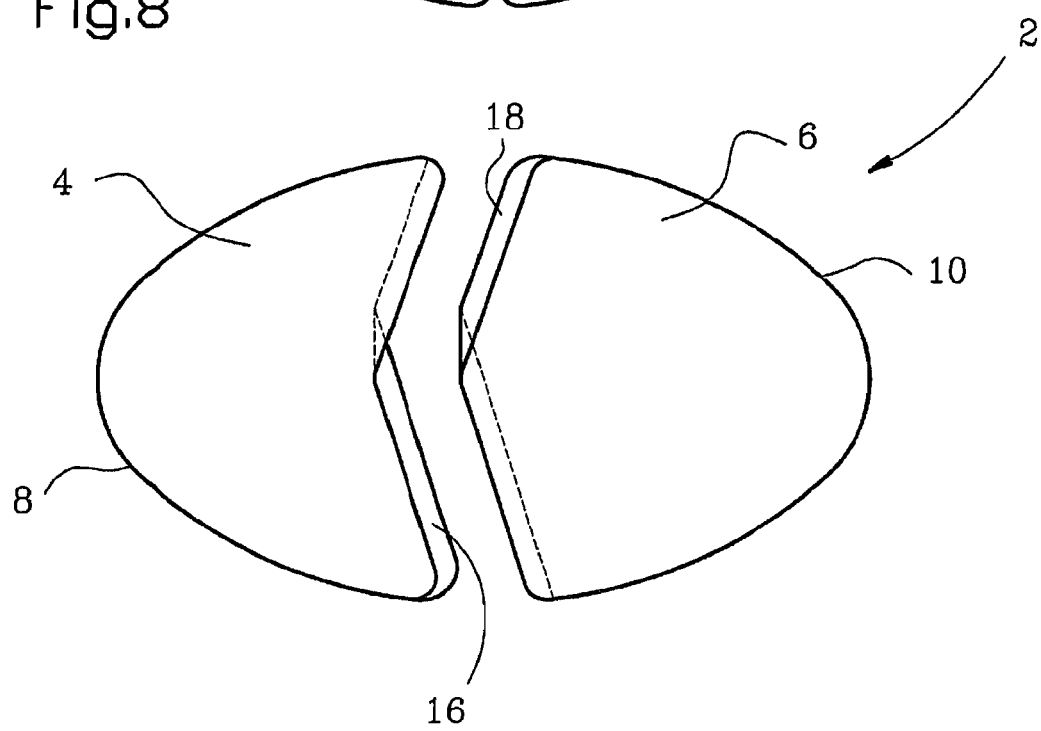

FIGS. 1-10 disclose pairs 2 of orthodontic retainer elements 4 and 6 according to prior art of Amundsen. Each such retainer element 4, 6 includes an oral surface 8 and 10, respectively; a dental attachment surface 12 and 14, respectively; and an approximal surface 16 and 18, respectively.

Figure 10:
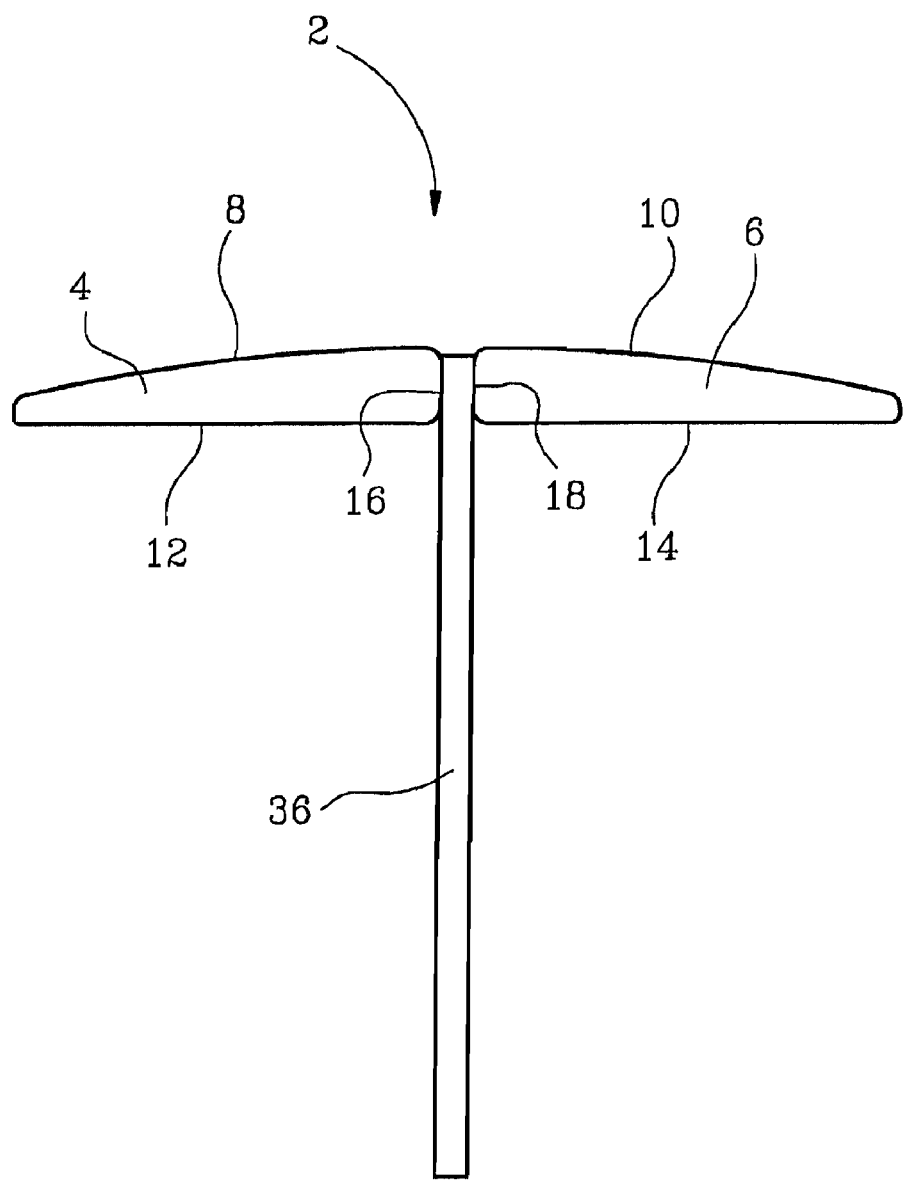
FIG. 10 shows a front view of the retainer elements of FIG. 5 releasably attached on either side of a guide strip, also as disclosed in prior art of Amundsen.

In FIG. 10, an approximal surface 16, 18 of a retainer element 4, 6 is attached on either side of a guide strip 36 according to prior art of Amundsen, and at one end thereof directly opposite to each other. As mentioned above, this attachment constellation of the retainer element 4, 6 to the guide strip 36 may cause some misalignment between the elements 4, 6 as they are released from the guide strip 36 and attached to corresponding teeth. This is a problem that the present invention seeks to remedy.

Figure 11:
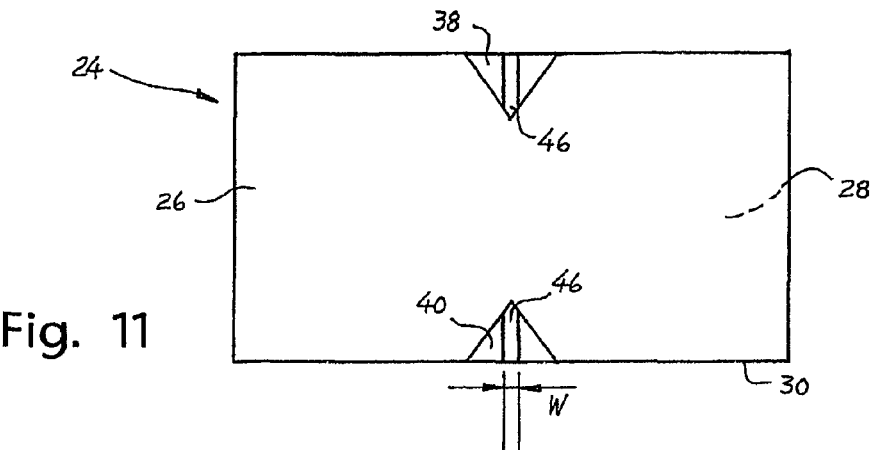
FIGS. 11 and 12 show two embodiments of the mounting jig according to the present invention, wherein the jig is in the form of a base.
Figure 12:
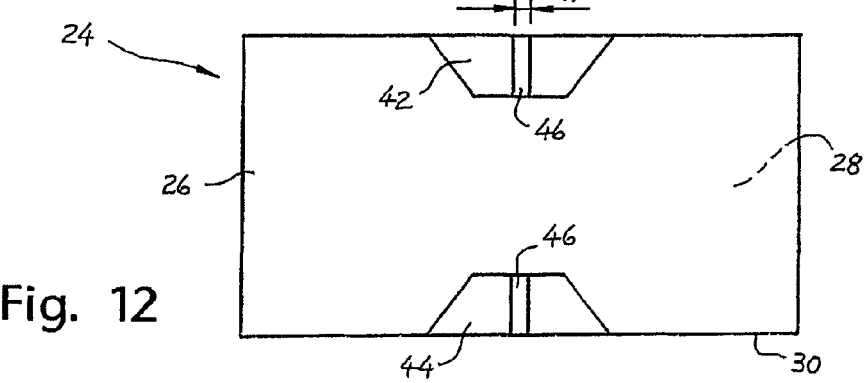

FIGS. 11 and 12 show a mounting jig in the form of a rectangular base 24, 124 comprising a dental side 26, 126; an oral side 28, 128; and a perimeter side 30, 130, respectively. Said dental side 26, 126 is also provided with two oppositely directed and tapered projections extending within the perimeter side 30, 130 of the base 24, 124. FIG. 11 shows triangular projections 38 and 40, whereas FIG. 12 shows trapezoidal projections 142 and 144. Such a projection does not have to be tapered and hence may be of another shape suitable for the purpose. In these embodiments, all projections 38, 40 and 142, 144 are positioned midways along the long sides of the rectangular base 24 and 124, respectively. Moreover, each projection 38, 40 and 142, 144 is provided with a groove 46, 46' and 146, 146', respectively, the grooves of which extend transversely relative to the direction of said long sides of the respective base 24, 124.

Figure 13:
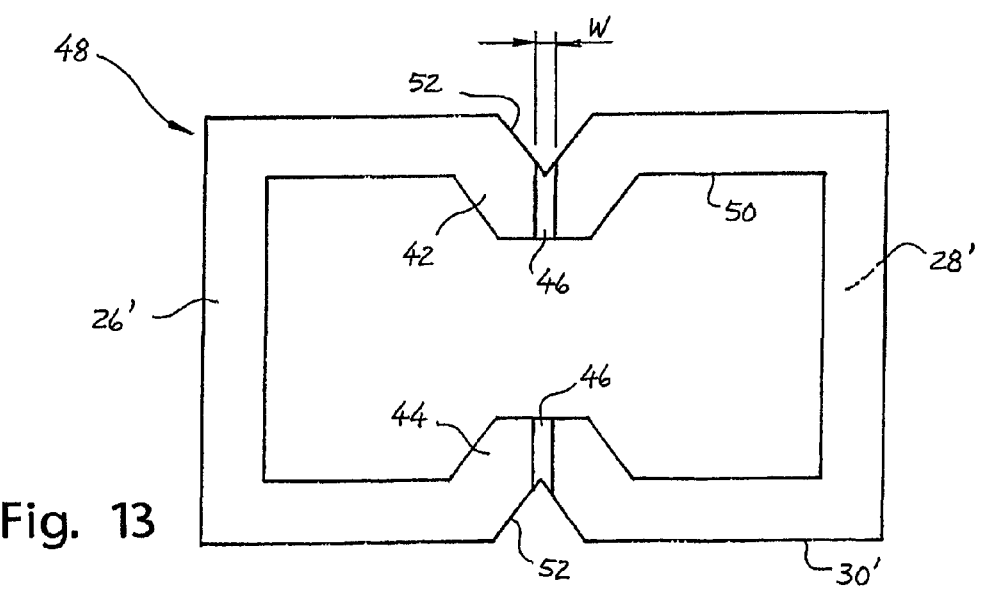
FIG. 13 shows an embodiment of the mounting jig according to the present invention, wherein the jig is in the form of a rim wall enclosure.

FIG. 13, however, shows a mounting jig in the form of a rim wall enclosure 248 comprising a perimeter side 230; an internal side 250; a dental side 226; and an oral side 228. Similar to the embodiment according to FIG. 12, the rim wall enclosure 248 is also provided with trapezoidal projections 242, 244, each having a respective groove 246, 246' provided thereto. Furthermore, said perimeter side 230 of the rim wall enclosure 248 is provided with an external recess 252, 252' positioned vis-à-vis each respective projection 242, 244.

Figure 14:
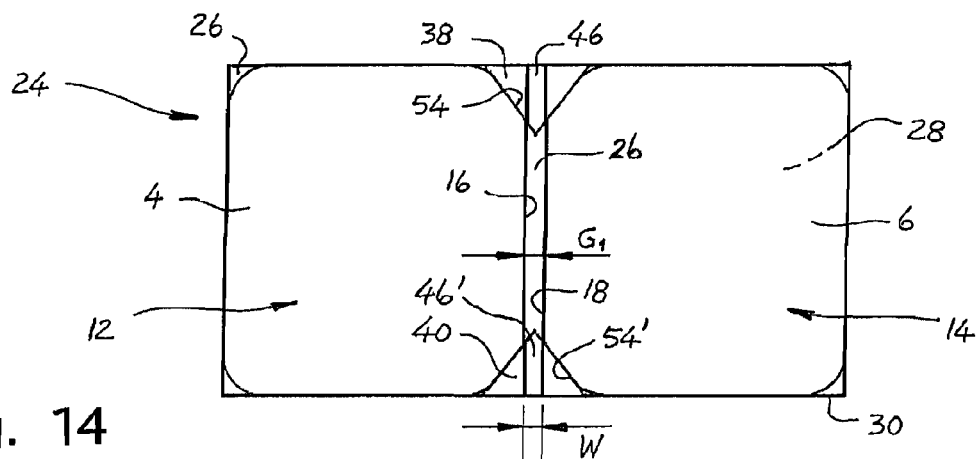
FIGS. 14-16 show the mounting jigs according to FIGS. 11-13, wherein each jig is provided with a pair of retainer elements each having a rounded, rectangular circumference shape.
Figure 15:
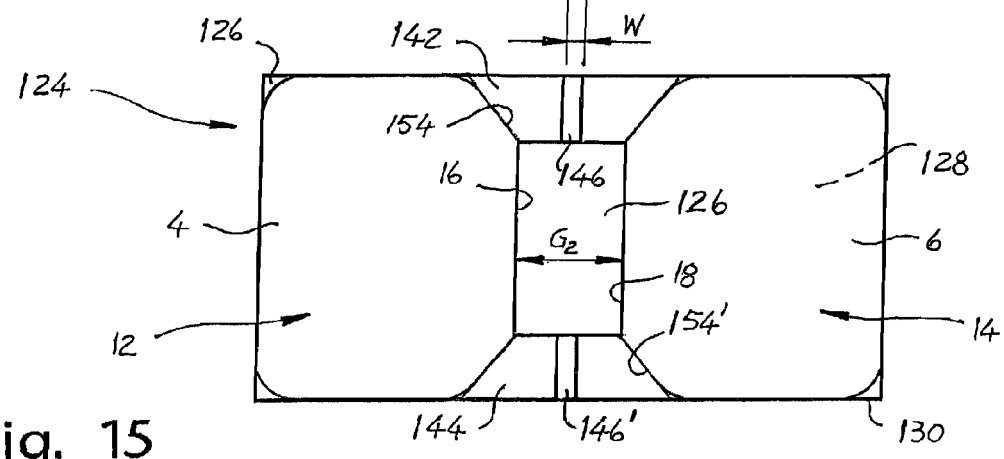
Figure 16:
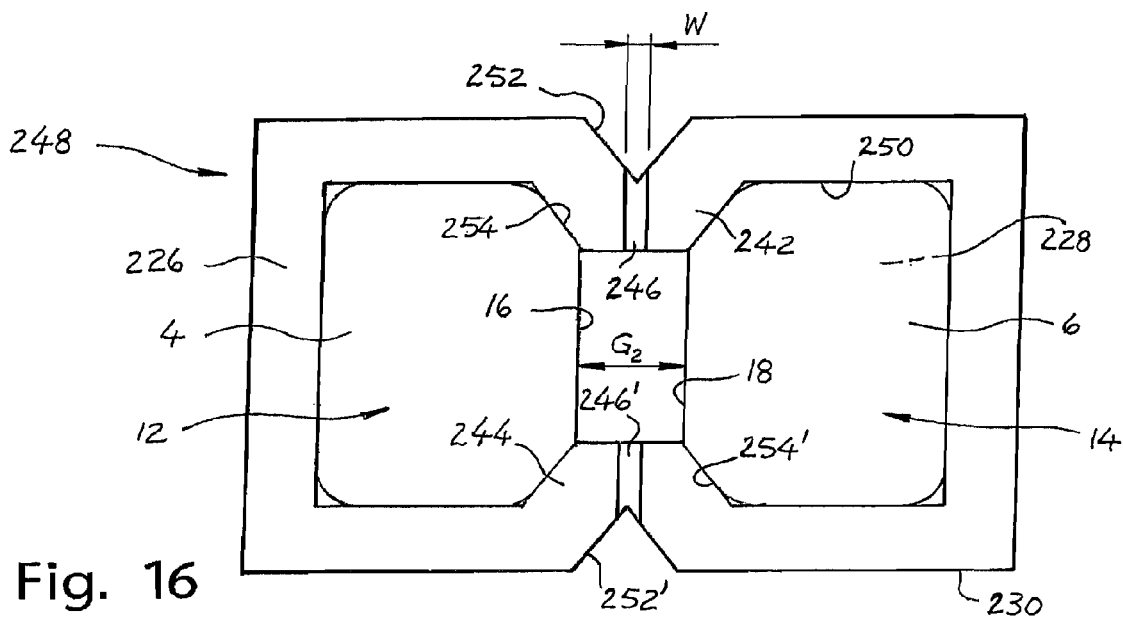

In FIGS. 14-16, each mounting jig shown in FIGS. 11-13 is provided with a pair 2 of retainer elements 4, 6, each having a rounded and rectangular circumference shape and a plane approximal surface 16, 18. The approximal surfaces 16, 18, however, may have any other complementary shapes suitable for specific orthodontic treatment of a patient. In the embodiments of FIGS. 14-16, said projections 38, 40; 142, 144; and 242, 244 assist in maintaining mechanically the retainer elements 4, 6, in a specific spatial relationship relative to each other. Each retainer element 4, 6 is provided with a respective bevel edge 54, 54'; 154, 154'; and 254, 254' on either side of an approximal surface 16, 18. Each bevel edge 54, 54'; 154, 154'; and 254, 254' engages a corresponding side of a projection 38, 40; 142, 144; and 242, 244, respectively. As mentioned above, retainer elements 4, 6 provided with such bevel edges 54, 54'; 154, 154'; and 254, 254' are instrumental in facilitating dental hygiene by allowing insertion of for example dental floss and alike between the elements 4, 6 and the teeth to which they are attached. A gap between the approximal surfaces 16, 18 of the two elements 4, 6 may be varied by selecting an appropriate shape, size and/or bevel angle of the projection and/or the approximal surface 16, 18 of a retainer element 4, 6. As such, a gap $G_1$ shown in FIG. 14 is substantially equal to a width W of said groove 46, 46' in the projections 38, 40, whereas a gap $G_2$ shown in FIGS. 15 and 16 is much larger than the width W of said groove 146, 146' and 246, 246' provided in the respective projections 142, 144 and 242, 244.

Figure 32:
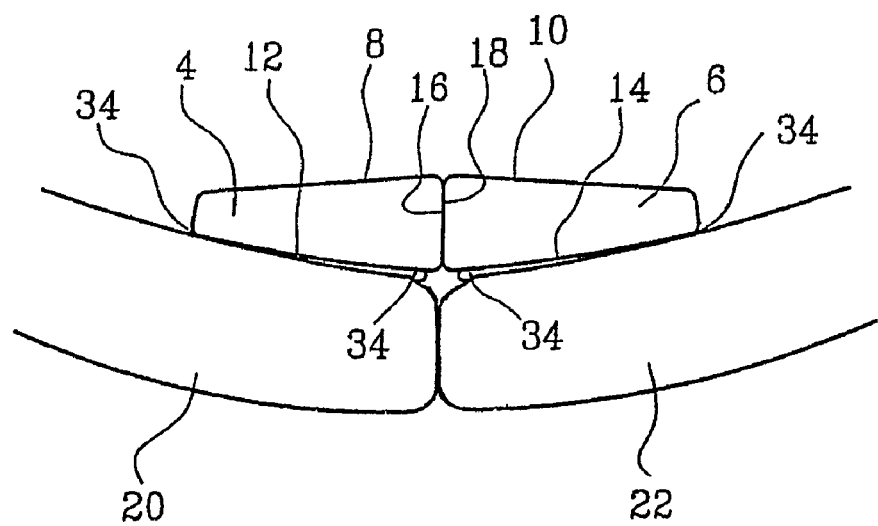
FIG. 32 shows an enlarged base view of a pair of adjacent teeth provided with a corresponding pair of retainer elements.

FIGS. 17-20 show a mounting jig in the form of a socket 356 comprising an assembly of a base 324 and a rim wall enclosure 348. Similar to the embodiment shown in FIGS. 13 and 16, the rim wall enclosure 348 is provided with external recesses 352, 352' positioned midways along the respective long sides of the enclosure 348. Vis-à-vis each recess 352, 352', the rim wall enclosure 348 is provided with two oppositely directed triangular projections 338, 340 extending within the enclosure 348. Moreover, each of the projections 338, 340 is provided with a respective groove 346, 346' of a width W extending transversely relative to the direction of said long sides of the enclosure 348, similar to that of the embodiments according to FIGS. 11-13. An enlarged view of the groove 346' is shown in FIG. 19. The rim wall enclosure 348 of the socket 356, however, is elevated midways along the long sides thereof, thereby forming an elevated midportion of the enclosure 348, cf. FIG. 18. Said elevated midportion serves to accommodate correspondingly shaped retainer elements 4, 6 within the inner space of the socket 356, said inner space confined by the base 324 and the rim wall enclosure 348. FIG. 32 shows an example of a pair 2 of such correspondingly shaped retainer elements 4, 6 after having been attached to a pair of adjacent teeth 20, 22 in a dental arch of a patient.

Figure 21:
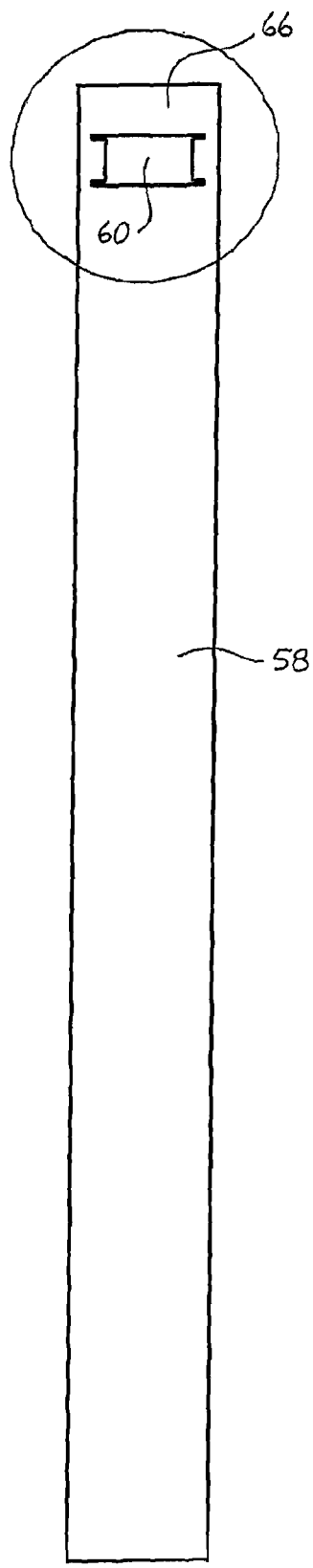
FIG. 21 shows a front view of a guide strip provided with a rectangular opening at one end thereof, within which opening the jig with its pair of retainer elements is to be inserted.
Figure 22:
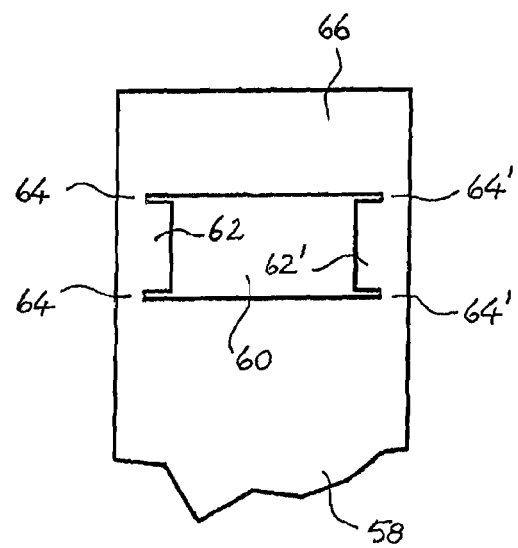
FIG. 22 shows the guide strip of FIG. 21 provided with two locking tabs extending into said rectangular opening therein.
Figure 23:
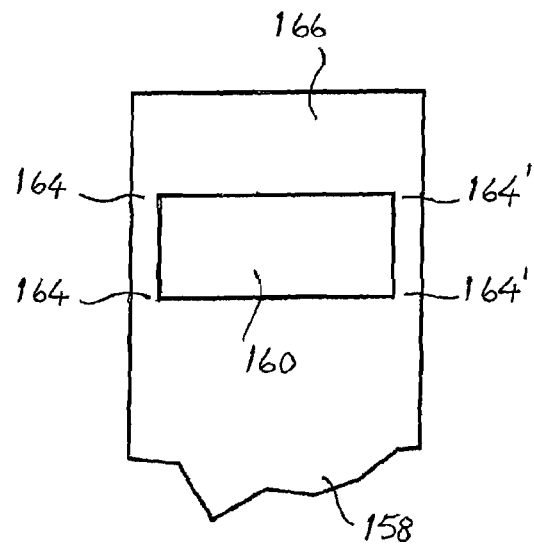
FIG. 23 shows a guide strip provided with a rectangular opening at one end thereof, said guide strip having no locking tabs extending into the opening therein.

FIGS. 21-23 show a suitable guide strip 58 or 158 to be used together with any of the above mounting jigs 24, 124, 248, 356 according to the invention. Said guide strip 58, 158 is provided with a respective rectangular opening 60, 160 at one end thereof, through which opening 60, 160 the jig and its releasably connected pair 2 of retainer elements 4, 6 is intended to be inserted prior to being attached to a corresponding pair of adjacent teeth. The guide strip 58 shown in FIG. 22 is provided with two locking tabs 62, 62' extending into the opening 60 from the short sides thereof, whereas the guide strip 158 shown in FIG. 23 is of a plain rectangular shape with no locking tabs 62, 62' provided thereto. By virtue of the opening 60, 160 provided in the guide strip 58, 158, respective weak zones 64, 64' and 164, 164' are also provided between the short sides of the opening 60, 160 and the edges of the respective guide strip 58, 158. The opening 60, 160 also divides the guide strip 58, 158 into a main body and a respective end piece 66, 166 at the end thereof.

Figure 24:
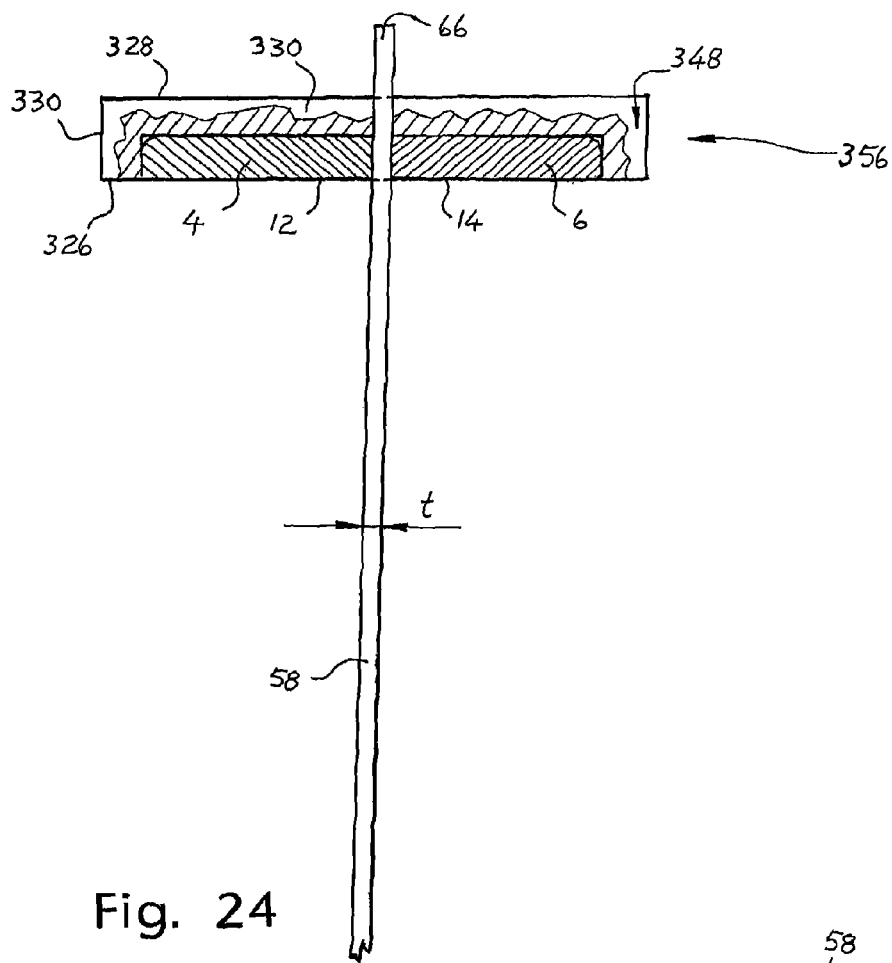
FIG. 24 shows a side view of the guide strip according to FIG. 21 having a socket jig inserted through the opening therein, wherein a cutout section of the socket shows one retainer element in a pair thereof positioned on either side of the guide strip.

FIG. 24 shows the guide strip 58 having a socket jig 356 inserted halfway through the rectangular opening 60 therein.

The opening 60 is also provided with two locking tabs 62, 62' similar to those shown in FIG. 22. A cutout section of FIG. 24 also shows the socket 356 provided with a retainer element 4, 6 positioned on either side of the guide strip 58. The guide strip 58 is of a thickness t substantially equal to said width W of the grooves 346, 346' provided on the dental side 326 of the jig's rim wall enclosure 348. Furthermore, the perimeter side 330 of the socket 356 is provided with external recesses 352, 352' similar to those shown in for example FIG. 20. When the socket 356 is inserted into the guide strip opening 60 as shown in FIG. 24, the locking tabs 62, 62' engage respective recesses 352, 352' in the socket 356. Simultaneously, the grooves 346, 346' in the socket 356 receive one long side of the rectangular opening 60 in the guide strip 58. The locking tabs 62, 62' and the respective grooves 346, 346' ensure that the socket jig 356 is positioned correctly with respect to the guide strip 58. They also ensure that each element 4, 6 in the socket 356 is positioned correctly with respect a corresponding tooth of said pair of adjacent teeth 20, 22 when being attached thereto.

Figure 25:
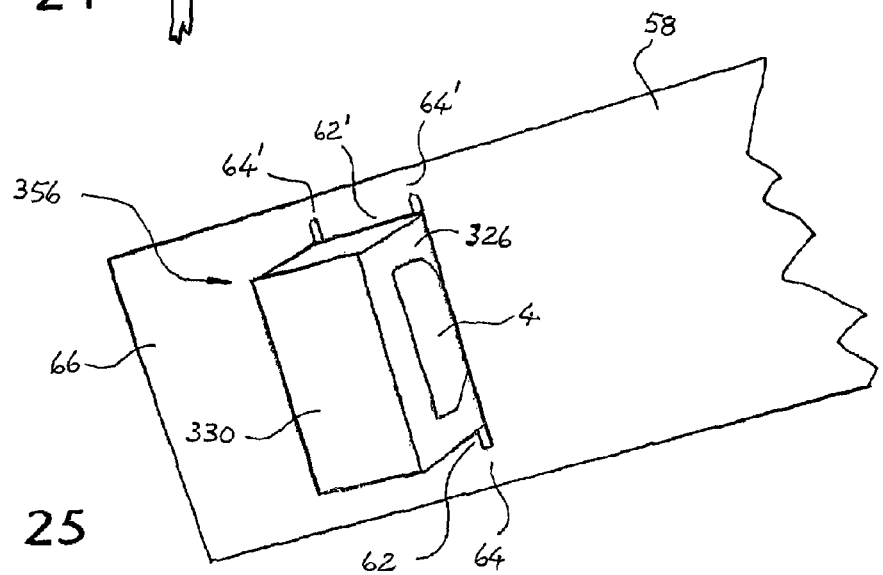
FIG. 25 shows a perspective view of one side of the guide strip according to FIG. 24, from which side one half of said socket extends whilst containing one retainer element of said pair thereof.

FIG. 25 shows a perspective view of one side of the guide strip 58 according to FIG. 24, in which the perspective view clearly shows retainer element 4 maintained mechanically in a specific position within the confines of one half of the socket 356. Said locking tabs 62, 62' are also clearly shown in FIG. 25.

Figure 26:
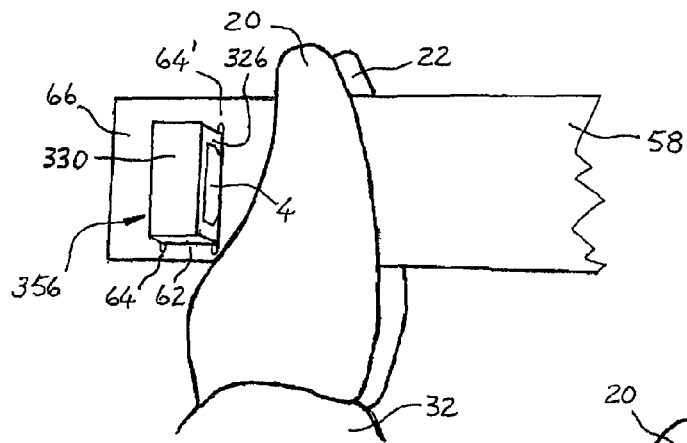
FIGS. 26-31 predominantly show perspective views of successive steps in using a jig according to the present invention for attaching a pair of retainer elements to a pair of adjacent teeth by using a guide strip.

FIGS. 26-31 illustrate successive steps in using the guide strip 58 with the releasably attached socket jig 356 of FIGS. 25-26 for attaching the pair 2 of retainer elements 4, 6 to said pair of adjacent teeth 20, 22 projecting from a gum 32.

In FIG. 26 the guide strip 58 is shown inserted between the teeth 20, 22 whilst maintaining the socket jig 356 at some distance from the teeth 20, 22.

Figure 27:
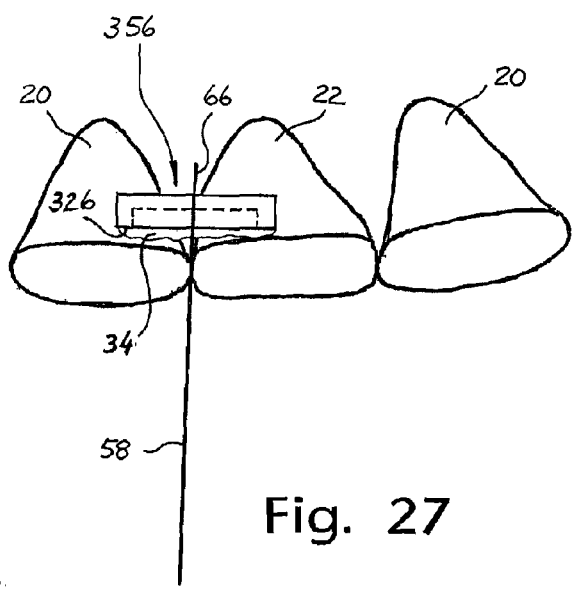

Plan view FIG. 27 shows the socket jig 356 still at some distance from the adjacent teeth 20, 22, but immediately after a layer 34 of a suitable bonding agent has been applied to the dental attachment surfaces 12, 14 of the retainer elements 4, 6. Due to the small size of the elements 4, 6 and the jig socket 356, some bonding agent will easily smear onto the dental side 326 of the socket 356, as illustrated in FIG. 27.

Figure 28:
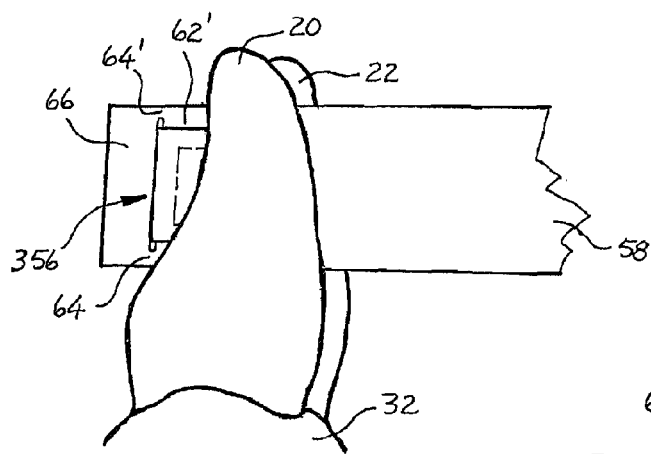

FIG. 28 shows the socket 356 and its contained elements 4, 6 provided with a layer 34 of said bonding agent (layer 34 not shown in this figure) after being pulled towards the adjacent teeth 20, 22 and placed directly against the teeth 20, 22. The intermediate layer 34 of the bonding agent is allowed to cure whilst in this position. Another neighboring tooth 22 is also shown for illustrative purposes.

Figure 29:
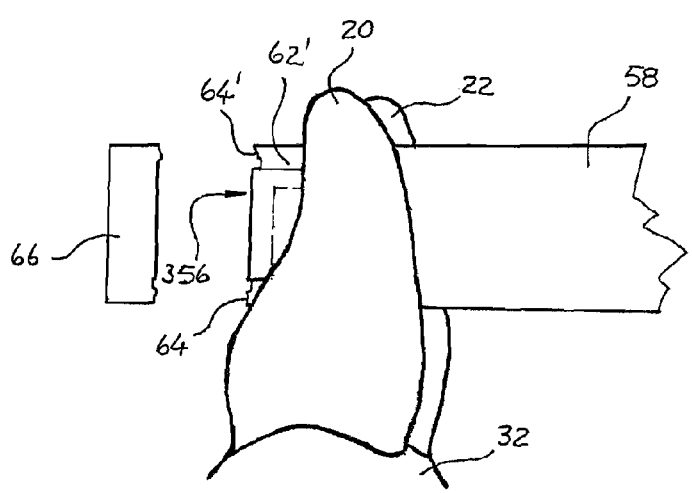

FIG. 29 illustrates the subsequent step, wherein said end piece 66 is broken away from the main body of the guide strip 58. For example, this may be achieved by flexing the end piece 66 back and forth about said weak zones 64, 64' of the guide strip 58. The flexing is continued until the material in the weak zones 64, 64' is fatigued and snaps, thereby allowing the end piece 66 to be removed, as shown in FIG. 29. The socket 356 may then be disconnected from the pair 2 of retainer elements 4, 6, which now are attached to the pair of adjacent teeth 20, 22, and removed therefrom. Any bonding agent material cured between the teeth 20, 22 and the dental side 326 of the socket 356 may be removed by means of ordinary dental tools.

Figure 30:
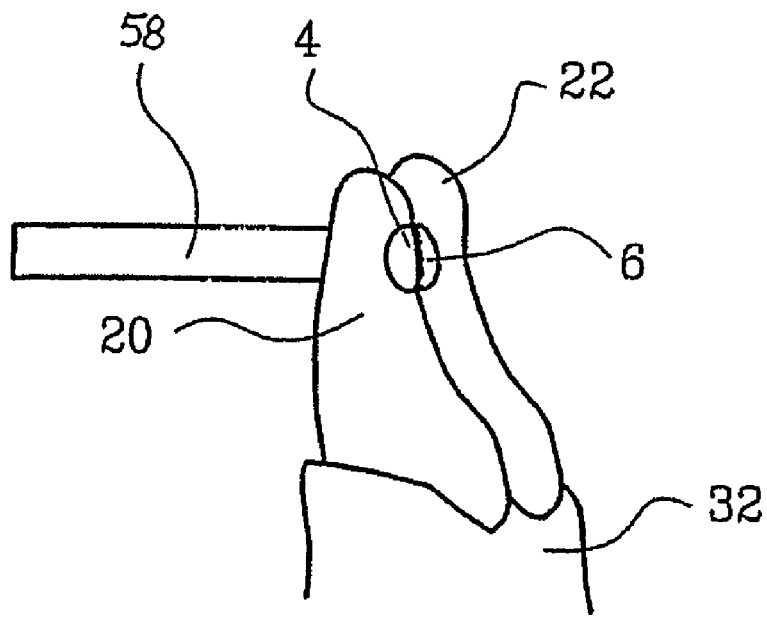
Figure 31:
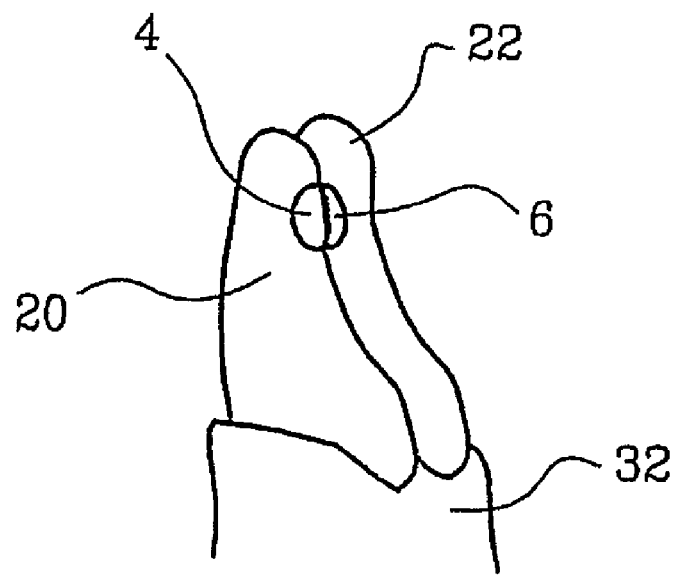

FIG. 30 shows a perspective view of the guide strip 58 when still positioned between the pair of adjacent teeth 20, 22, but immediately after having removed the end piece 66 from the main body thereof, and immediately after having removed the socket 356 from the retainer elements 4, 6. FIG. 31 shows the same perspective view, but after the guide strip 58 has been removed from the teeth 20, 22.

FIG. 32 is an enlarged base view of the pair of adjacent teeth 20, 22 having the pair 2 of retainer elements 4, 6 attached thereto. In this position of use, the dental attachment surfaces 12, 14 of the elements 4, 6 are attached to the teeth 20, 22 by means of said intermediate layer 34 of bonding agent. In this position, the approximal surfaces 16, 18 of the elements 4, 6 are in contact and mutually cooperate to support and stabilize each other, thus also stabilizing the pair of adjacent teeth 20, 22. Although mutually engaging each other, the retainer elements 4, 6 still are separate from each other. This feature may be used to advantage to promote dental hygiene with a patient. Due to the physiological mobility and resiliency of the teeth 20, 22 within their gum 32, the pair of teeth 20, 22 and their securely attached retainer elements 4, 6 therefore will temporarily move apart laterally in response to temporarily inserting dental floss, for example.

Figure 33:
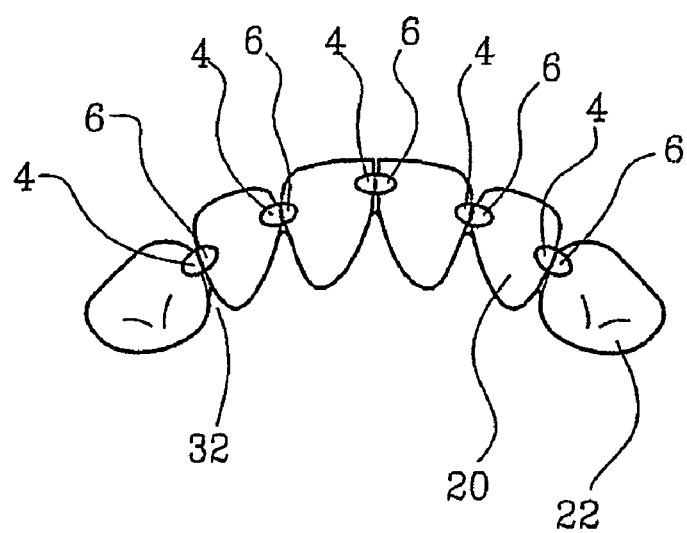
FIG. 33 shows a plan view of several cooperating pairs of retainer elements aligned successively in a retention segment along the mandible, thereby stabilizing successive teeth in a mandible of a patient.

FIG. 33 shows several cooperating pairs 2 of retainer elements 4, 6 aligned successively in a retention segment along a mandible of a patient to stabilize successive pairs of adjacent teeth 20, 22 thereof.

The invention claimed is:

1. An apparatus for retention of teeth in a dental arch during passive orthodontic treatment of a patient, the apparatus comprising:
    a pair of orthodontic retainer elements structured to attach to a pair of adjacent teeth in the dental arch, each retainer element comprising a dental attachment surface, an approximal surface, and an oral surface;
    wherein the dental attachment surface of one retainer element in the pair of retainer elements is structured to attach to one tooth in the pair of adjacent teeth, whereas the dental attachment surface of the other retainer element in the pair of retainer elements is structured to attach to the other tooth in the pair of adjacent teeth; and
    wherein at least one portion of the approximal surface of the one retainer element is formed complementary to at least one portion of the approximal surface of the other retainer element, the respective approximal surfaces thus forming contact surfaces configured to mate and stabilize the pair of retainer elements when the pair of retainer elements is attached to the pair of adjacent teeth, thereby stabilizing the pair of adjacent teeth; and
    a mounting jig that is releasably connected to the pair of retainer elements and temporarily holds the pair retainer elements in a predetermined opposed spatial relationship, the predetermined spatial relationship allowing the contact surfaces to properly mate when the pair of opposed retainer elements are mounted on the pair of adjacent teeth and the mounting jig is removed from the pair of retainer elements;
    wherein the mounting jig comprises a perimeter side that defines a recess that is sized to engage with a locking tab on a guide strip structured for insertion between the pair of adjacent teeth in order to attach the pair of opposed retainer elements to the pair of adjacent teeth.

2. The apparatus according to claim 1, wherein a gap having a predetermined width exists between the respective approximal surfaces when the pair of retainer elements are held by the mounting jig.

3. An apparatus for retention of teeth in a dental arch during passive orthodontic treatment of a patient, the apparatus comprising:
    a pair of orthodontic retainer elements structured to attach to a pair of adjacent teeth in the dental arch, each retainer element comprising a dental attachment surface, an approximal surface, and an oral surface;

wherein the dental attachment surface of one retainer element in the pair of retainer elements is structured to attach to one tooth in the pair of adjacent teeth, whereas the dental attachment surface of the other retainer element in the pair of retainer elements is structured to attach to the other tooth in the pair of adjacent teeth; and wherein at least one portion of the approximal surface of the one retainer element is formed complementary to at least one portion of the approximal surface of the other retainer element, the respective approximal surfaces thus forming contact surfaces configured to mate and stabilize the pair of retainer elements when the pair of retainer elements is attached to the pair of adjacent teeth, thereby stabilizing the pair of adjacent teeth; and a mounting jig that is releasably connected to the pair of retainer elements and temporarily holds the pair retainer elements in a predetermined opposed spatial relationship, the predetermined spatial relationship allowing the contact surfaces to properly mate when the pair of opposed retainer elements are mounted on the pair of adjacent teeth and the mounting jig is removed from the pair of retainer elements;

wherein the mounting jig comprises a perimeter side and at least one projection that extends inwardly from the perimeter side and releasably engages with a beveled edge on each of the retainer elements in the pair thereof, thereby temporarily holding the pair of retainer elements in the opposed spatial relationship.

4. The apparatus according to claim 3, wherein the at least one projection is tapered.

5. The apparatus according to claim 3, wherein the at least one projection is trapezoidal.

6. The apparatus according to claim 3, wherein a gap having a predetermined width exists between the respective approximal surfaces when the pair of retainer elements are held by the mounting jig.

7. An apparatus for retention of teeth in a dental arch during passive orthodontic treatment of a patient, the apparatus comprising:

a pair of orthodontic retainer elements structured to attach to a pair of adjacent teeth in the dental arch, each retainer element comprising a dental attachment surface, an approximal surface, and an oral surface;

wherein the dental attachment surface of one retainer element in the pair of retainer elements is structured to attach to one tooth in the pair of adjacent teeth, whereas the dental attachment surface of the other retainer element in the pair of retainer elements is structured to attach to the other tooth in the pair of adjacent teeth; and wherein at least one portion of the approximal surface of the one retainer element is formed complementary to at least one portion of the approximal surface of the other retainer element, the respective approximal surfaces thus forming contact surfaces configured to mate and stabilize the pair of retainer elements when the pair of retainer elements is attached to the pair of adjacent teeth, thereby stabilizing the pair of adjacent teeth; and a mounting jig that is releasably connected to the pair of retainer elements and temporarily holds the pair retainer elements in a predetermined opposed spatial relationship, the predetermined spatial relationship allowing the contact surfaces to properly mate when the pair of opposed retainer elements are mounted on the pair of adjacent teeth and the mounting jig is removed from the pair of retainer elements;

wherein the mounting jig comprises a base having a dental side, an oral side and a perimeter side, wherein the dental side of the base is releasably connected to at least one portion of the oral surface of each retainer element in the pair of opposed retainer elements.

8. The apparatus according to claim 7, wherein the mounting jig comprises a rim wall enclosure having a perimeter side, an internal side, a dental side, and an oral side, wherein the rim wall enclosure is releasably connected to at least one portion of the oral surface of each retainer element in the pair of opposed retainer elements, and further comprising a socket formed from an assembly of the base and the rim wall enclosure, wherein the rim wall enclosure projects from the dental side of the base.

9. The apparatus according to claim 8, wherein a projection extends inwardly from the rim wall enclosure and releasably engages with a beveled edge on each of the retainer elements in the pair thereof, thereby temporarily holding the pair of retainer elements in the opposed spatial relationship.

10. The apparatus according to claim 9, wherein the rim wall enclosure comprises long sides having an elevated midportion.

11. The apparatus according to claim 9, wherein the rim wall enclosure defines an inner space and is structured to accommodate correspondingly shaped opposed retainer elements within the inner space.

12. The apparatus according to claim 8, wherein the perimeter side of the rim wall enclosure defines a recess that is sized to engage with a locking tab on a guide strip structured for insertion between the pair of adjacent teeth in order to attach the pair of opposed retainer elements to the pair of adjacent teeth.

13. The apparatus according to claim 12, wherein the recess is positioned between the approximal surface portions of the opposed retainer elements.

14. The apparatus according to claim 7, wherein a gap having a predetermined width exists between the respective approximal surfaces when the pair of retainer elements are held by the mounting jig.

15. An apparatus for retention of teeth in a dental arch during passive orthodontic treatment of a patient, the apparatus comprising:

a pair of orthodontic retainer elements structured to attach to a pair of adjacent teeth in the dental arch, each retainer element comprising a dental attachment surface, an approximal surface, and an oral surface;

wherein the dental attachment surface of one retainer element in the pair of retainer elements is structured to attach to one tooth in the pair of adjacent teeth, whereas the dental attachment surface of the other retainer element in the pair of retainer elements is structured to attach to the other tooth in the pair of adjacent teeth; and wherein at least one portion of the approximal surface of the one retainer element is formed complementary to at least one portion of the approximal surface of the other retainer element, the respective approximal surfaces thus forming contact surfaces configured to mate and stabilize the pair of retainer elements when the pair of retainer elements is attached to the pair of adjacent teeth, thereby stabilizing the pair of adjacent teeth; and a mounting jig that is releasably connected to the pair of retainer elements and temporarily holds the pair retainer elements in a predetermined opposed spatial relationship, the predetermined spatial relationship allowing the contact surfaces to properly mate when the pair of opposed retainer elements are mounted on the pair of adjacent teeth and the mounting jig is removed from the pair of retainer elements;

wherein the mounting jig comprises a rim wall enclosure having a perimeter side, an internal side, a dental side, and an oral side, wherein the rim wall enclosure is releasably connected to at least one portion of the oral surface of each retainer element in the pair of opposed retainer elements.

16. The apparatus according to claim 15, wherein a projection extends inwardly from the rim wall enclosure and releasably engages with a beveled edge on each of the retainer elements in the pair thereof, thereby temporarily holding the pair of retainer elements in the opposed spatial relationship.

17. The apparatus according to claim 16, wherein the rim wall enclosure comprises long sides having an elevated midportion.

18. The apparatus according to claim 16, wherein the rim wall enclosure defines an inner space and is structured to accommodate correspondingly shaped opposed retainer elements within the inner space.

19. The apparatus according to claim 15, wherein the perimeter side of the rim wall enclosure defines a recess that is sized to engage with a locking tab on a guide strip structured for insertion between the pair of adjacent teeth in order to attach the pair of opposed retainer elements to the pair of adjacent teeth.

20. The apparatus according to claim 19, wherein the recess is positioned between the approximal surface portions of the opposed retainer elements.

21. The apparatus according to claim 15, wherein a gap having a predetermined width exists between the respective approximal surfaces when the pair of retainer elements are held by the mounting jig.

22. An apparatus for retention of teeth in a dental arch during passive orthodontic treatment of a patient, the apparatus comprising:

a pair of orthodontic retainer elements structured to attach to a pair of adjacent teeth in the dental arch, each retainer element comprising a dental attachment surface, an approximal surface, and an oral surface;

wherein the dental attachment surface of one retainer element in the pair of retainer elements is structured to attach to one tooth in the pair of adjacent teeth, whereas the dental attachment surface of the other retainer element in the pair of retainer elements is structured to attach to the other tooth in the pair of adjacent teeth; and wherein at least one portion of the approximal surface of the one retainer element is formed complementary to at least one portion of the approximal surface of the other retainer element, the respective approximal surfaces thus forming contact surfaces configured to mate and stabilize the pair of retainer elements when the pair of retainer elements is attached to the pair of adjacent teeth, thereby stabilizing the pair of adjacent teeth; and a mounting jig that is releasably connected to the pair of retainer elements and temporarily holds the pair retainer elements in a predetermined opposed spatial relationship, the predetermined spatial relationship allowing the contact surfaces to properly mate when the pair of opposed retainer elements are mounted on the pair of adjacent teeth and the mounting jig is removed from the pair of retainer elements;

wherein a dental side of the mounting jig defines a groove that is sized to engage and interlock with an opening provided in a guide strip structured for insertion between the adjacent teeth in order to attach the pair of opposed retainer elements to the pair of adjacent teeth.

23. The apparatus according to claim 22, wherein the groove has with a width that is substantially equal to a thickness of the guide strip.

24. The apparatus according to claim 22, wherein a gap having a predetermined width exists between the respective approximal surfaces when the pair of retainer elements are held by the mounting jig.

* * * * *